United States Patent [19]

Maeda et al.

[11] Patent Number: 5,030,090
[45] Date of Patent: Jul. 9, 1991

[54] OPTICAL TOOTHBRUSH AND METHOD OF USE

[75] Inventors: Tetsuo Maeda, Osaka; Koichi Imanaka, Kyoto, both of Japan

[73] Assignee: Omron Corporation, Kyoto, Japan

[21] Appl. No.: 504,807

[22] Filed: Apr. 5, 1990

[30] Foreign Application Priority Data

Aug. 14, 1989 [JP] Japan .................................. 64-209757

[51] Int. Cl.⁵ .......................... A61C 1/00; A61C 3/00; A61C 15/00
[52] U.S. Cl. ........................................ 433/29; 433/216
[58] Field of Search ................. 433/29, 215, 216, 229; 15/167.1

[56] References Cited

U.S. PATENT DOCUMENTS 4,273,535 6/1981 Yamamoto et al. ................ 433/216
4,779,173 10/1988 Carr et al. ........................... 362/109

Primary Examiner—John J. Wilson
Assistant Examiner—Cindy A. Cherichetti
Attorney, Agent, or Firm—Fish & Richardson

[57] ABSTRACT

An optical toothbrush used for medical treatment comprises a plurality of narrow fibers connected to a light generating device and extending through a brush base, wherein the fibers are bent to form an L-shape and project outwardly from the base to form a brush. Light emitted from the light generating device is guided into each fiber at its base and projected through the brush tips to provide oral hygiene.

19 Claims, 1 Drawing Sheet

OPTICAL TOOTHBRUSH AND METHOD OF USE

BACKGROUND

1. Field of the Invention

This invention relates to a new development in oral hygiene which involves the use of a semiconductor laser or a LED. Scientific studies have determined that gingivitis and other oral diseases can be treated and even prevented by directing such a light source to the diseased area. Specifically, projection of a continuation wave or a pulse wave towards a diseased area has been found to reduce pain, inflammation, and improve blood circulation. However, while the medicinal effect is known, the cause is still a mystery and is being studied. Scientific studies regarding the cause of the curative effect have to date explored photochemical reaction, photoacoustic effect, and electromagnetic effect. One day science will probably determine the cause of the phenomenenon, but for the purposes of this invention, it is enough to know the effect.

2. Related Art

Unexamined Japanese publication 57-200210 discloses a laser handpiece that is used by a dentist for applying medical treatment to teeth and gums by utilizing the light projected from the laser. According to this laser handpiece, shown in FIG. 4, a laser guide fiber 12 is inserted into a hollow tube provided in a handle 11 of the instrument. Furthermore, the laser guide fiber 12 is bent to form a L-shaped tip. Housed in this L-shaped tip portion is a converging lens 13.

Discussing operation of the laser handpiece, a laser beam is emitted from a laser light source (not shown) and directed into the laser guide fiber 12. The laser beam is then emitted from the tip of the laser guide fiber 12, but first it is converged by the converging lens 13. The emitted light is most intensified at the focal point of the converging lens 13, which, ideally, demarcates the diseased portion of the teeth or gums.

However, this laser handpiece has several practical limitations. First, the laser guide fiber 12 is formed singularly so that treatment of diseased portions is limited to a small area each time. Thus, medical treatment with the instrument lacks efficiency. Secondly, it is very difficult to mount the converging lens 13 at the tip of the laser guide fiber 12. Accordingly, the mounting cost is high. Further adding to the cost is the converging lens 13 itself which is very small and special and, thus, expensive. Finally, this instrument is designed for exclusive use by a dentist and is not designed or expected to be used for normal, everyday use by an average household. Accordingly, the device is also not designed for preventive use as the dentist only uses the instrument for treatment purposes.

SUMMARY

This invention was conceived in view of the foregoing problems. Therefore, an objective of this invention is to make it possible to simultaneously provide medical treatment to a plurality of diseased parts. To this end, not one but a plurality of optical fibers are provided.

Another objective is to provide an optical apparatus that is less costly to construct. Therefore, the expensive converging lens has been eliminated.

Yet another objective is to provide such an apparatus that is practical. To achieve this goal, an apparatus is provided that is designed for everyday use at home by an average person; no special skills are needed to operate the apparatus.

A further objective is to provide a practical optical apparatus that is desirable to use. Therefore, the optical apparatus according to this invention has been incorporated into a toothbrush. With this invention, a consumer can clean his teeth as always with the added benefit of preventing and treating teeth and gum disease. Also, use of the device will be easy to habituate as it will no doubt be associated with the common task of brushing one's teeth.

The above objects are realized by the following structure. The optical toothbrush according to this invention comprises a bundle of narrow, transparent fibers, a light generating device provided at the base end of the bundle of fibers, and a brush base for containing the fibers, wherein the fibers are bent to form an L-shape extending outwardly from the brush base to form a brush. Light emitted from the light generating device is guided into each fiber at the base portion and illuminated onto the diseased portions through the brush tips.

Other objects and advantages of this invention will become apparent from the following description and accompanying drawings.

DESCRIPTION OF THE PREFERRED EMBODIMENT

Figure 1:
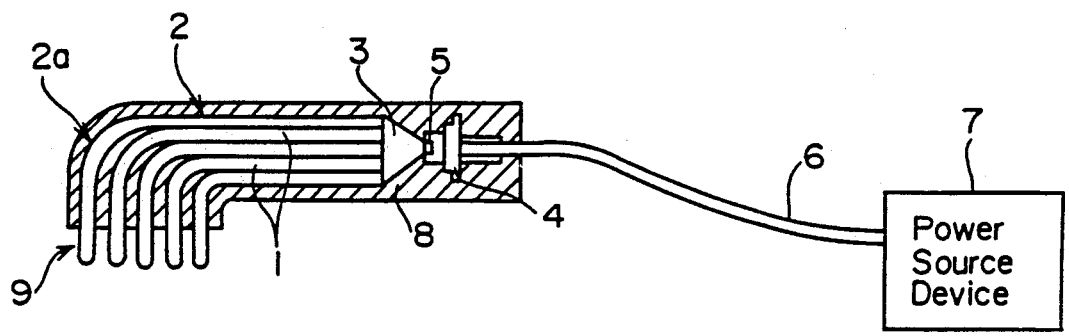
FIG. 1 is a partially cross-sectional view of one embodiment of an optical toothbrush according to this invention.

In the first embodiment of this invention, shown in FIG. 1, a plurality of narrow phototransparent fibers 1 are bundled together to make a narrow fiber bundle 2. Furthermore, each transparent fiber 1 has provided on its outer portion a thin metal layer which has the function of reflecting internal light travelling through each fiber to prevent loss of the light. The base part of the narrow fiber bundle 2 is connected to the base portion of a cone-shaped connecter 3, which is composed of quartz glass. Semiconductor laser 5 serves as a light generating device and is mounted on stem 4. Furthermore, the semiconductor laser's 5 illuminating end is connected to the vertex of the cone-shaped connecter 3. Also, an electrode terminal of the semiconductor laser 5 projects from the stem 4 and is connected to a power source device 7 through a power supply cord 6.

Figure 2:
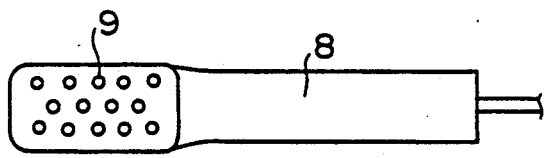
FIG. 2 is a partial bottom view of the toothbrush in FIG. 1.

At the end of the narrow fiber bundle 2, each narrow fiber 1 is separated in a diverging direction and folded, forming a bent portion 2a. Almost all the parts of the apparatus, including the narrow fiber bundle 2, the cone-shaped connecter 3, the stem 4, and the semiconductor laser 5, are molded by a resin which constitutes a brush base s. However, the tip of bent portion 2a extends outside of the brush base 8 and forms a brush 9, as can be seen in FIG. 2.

When turning on the power source 7, exciting energy is supplied through the power supply cord 6 to the semiconductor laser 5 so that a laser beam in the form of a continuation wave or a pulse wave is emitted from the semiconductor laser 5. This laser beam is transformed while travelling through the cone-shaped connecter 3 and, as a result, enters each narrow fiber 1 that constitutes the narrow fiber bundle 2. As the light travels through each fiber 1, it is continually reflected inside the fiber 1 due to the surrounding metal layer. Therefore, light is conveyed to the brush 9 and emitted at the tip thereof.

The laser beam is transferred to the narrow fiber bundle 2 without loss because the cone-shaped connecter 3 is firmly placed between the semiconductor laser 5 and the bundle 2. Thus, loss is eliminated because no light can escape the structure.

The apparatus according to this invention is used in the same manner one would use a normal toothbrush. An operator handles the brush base s to manipulate the brush 9 into the mouth and then brushes his teeth and gums, keeping the brush tips 9, and thus the emitted light, directed towards the teeth and gums. Since the brush 9 comprises many narrow fibers 1, a large area of the mouth can be treated with the emitted light at one time. Thus, pain and inflammation can be efficiently reduced in the diseased areas while blood circulation can also be improved in other locations, thus aiding in prevention of oral diseases.

Figure 3:
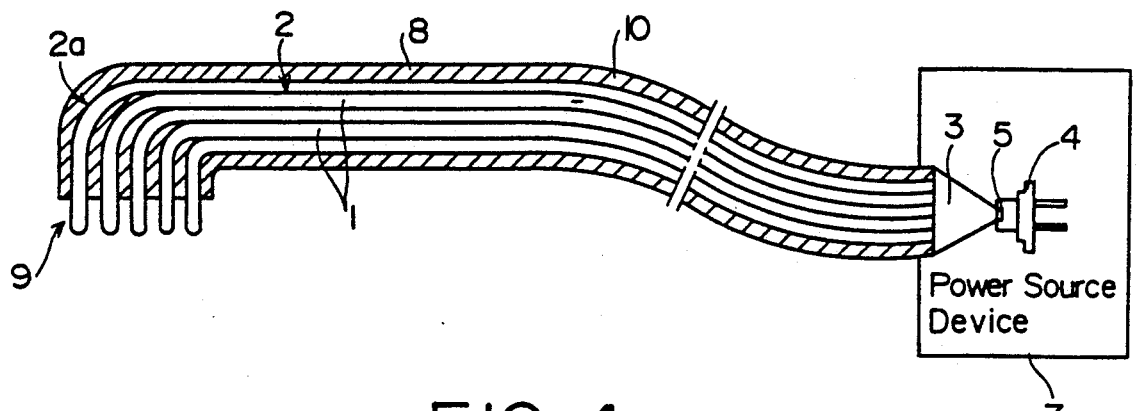
FIG. 3 is a partial cross-sectional view of another embodiment of an optical toothbrush according to this invention.
Figure 4:
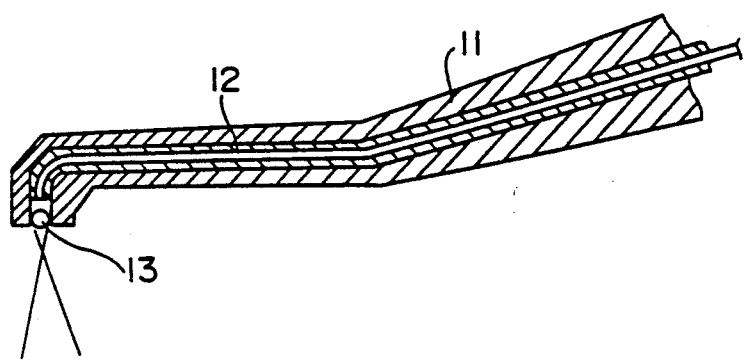
FIG. 4 is a cross-sectional view of a dentist's laser handpiece.

As illustrated in FIG. 3, another embodiment of this invention has a power source 7 which includes a light generating device. A stem 4, a semiconductor laser 5, and a cone-shaped connecter 3 are all contained within the casing of the power source 7. An elongated narrow fiber bundle 2 is firmly connected to the cone-shaped connecter 3. However, in this embodiment, the narrow fiber bundle 2 is originally contained in a flexible cord 10 which is made of a molded soft resin that is flexible in order to withstand stress put on the narrow fiber bundle 2 during brushing. In addition to molded resin, a flexible metal bellows could comprise the flexible cord 10. The rest of the embodiment is the same as in FIG. 1, so the same explanation applies.

Comparing the merits of the two embodiments, the first embodiment, with the light generating device 5 contained in the brush base 8, enables the length of the narrow fiber bundle 2 to be shortened. This reduces the cost of the apparatus because optical fibers are expensive. However, the second embodiment may be sturdier due to the more flexible structure provided by the cord 10.

The above descriptions and accompanying drawings are merely illustrative of the applications of the principles of the present invention and are not limiting. Many other embodiments falling under the spirit and scope of this invention may be devised by those skilled in the art. Accordingly, this invention is only limited by the scope of the appended claims.

What is claimed is:

1. An optical toothbrush, comprising:
    a plurality of narrow optical fibers;
    a light generating device comprising a semiconductor laser provided at a base portion of said plurality of fibers; and
    a brush base for firmly holding said fibers, wherein the fibers are bent in an L-shape and the tip of each fiber projects outwardly from the brush base to form a brush, and
    wherein said optical fibers direct the light from said light generating device toward the teeth and surrounding tissue of a user for therapeutic purposes.

2. An optical toothbrush according to claim 1, wherein the narrow optical fibers are transparent and are encompassed by a thin metal layer that reflects light traveling therethrough.

3. An optical toothbrush according to claim 1, wherein the light generating device generates a continuous wave.

4. An optical toothbrush according to claim 1, wherein the light generating device is connected to a power source by a power supply cord.

5. An optical toothbrush according to claim 1, wherein the light generating device is contained in a casing of a power source.

6. An optical toothbrush according to claim 5, wherein the narrow fibers projecting from the light generating device are contained in a flexible cord.

7. An optical toothbrush, comprising:
    a plurality of narrow optical fibers;
    a pulse wave light generating device provided at a base portion of said plurality of fibers; and
    a brush base for firmly holding said fibers, wherein the fibers are bent in an L-shape and the tip of each fiber projects outwardly from the brush base to form a brush,
    wherein said optical fibers direct the light from said light generating device toward the teeth and surrounding tissue of a user for therapeutic purposes.

8. An optical toothbrush according to claim 7, wherein the fibers are connected to the light generating device by a cone-shaped connector.

9. An optical toothbrush according to claim 8, wherein the cone-shaped connector is made out of quartz glass.

10. An optical toothbrush according to claim 7, wherein the pulse wave light generating device comprises a semiconductor laser.

11. An optical toothbrush according to claim 7, wherein the narrow optical fibers are transparent and are encompassed by a thin metal layer that reflects light traveling therethrough.

12. An optical toothbrush according to claim 7, wherein the fibers are connected to the light generating device by a cone-shaped connector.

13. An optical toothbrush according to claim 12, wherein the cone-shaped connector is made out of quartz glass.

14. An optical toothbrush according to claim 7, wherein the pulse wave light generating device is contained in a casing of a power source.

15. An optical toothbrush according to claim 7, wherein the narrow fibers projecting from the light generating device are contained in a flexible cord.

16. A method for therapeutically treating teeth and surrounding tissue with light, comprising the steps of:
    providing an optical toothbrush comprising a plurality of narrow optical fibers firmly held in a brush base and bent in an L-shape with the tip of each fiber projecting outwardly from the brush base to form a brush;
    shining a light source into said optical fibers at the base portion of said fibers; and
    brushing the teeth and surrounding tissue with said optical toothbrush to illuminate, and thereby provide a therapeutic effect to, the teeth and surrounding tissue.

17. The method according to claim 16 wherein said shining step includes pulsing said light source to produce a pulsed light wave.

18. The method according to claim 16 wherein said shining step includes continuously shining said light to produce a continuous light wave.

19. The method according to claim 16 wherein said shining step includes shining light from a semiconductor laser source.

* * * * *